United States Patent
Liu

(10) Patent No.: US 10,369,381 B2
(45) Date of Patent: Aug. 6, 2019

(54) SYSTEM AND METHOD FOR ROBUST INTENSITY-MODULATED PROTON THERAPY PLANNING

(71) Applicant: MAYO FOUNDATION FOR MEDICAL EDUCATION AND RESEARCH, Rochester, MN (US)

(72) Inventor: Wei Liu, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 620 days.

(21) Appl. No.: 14/843,384

(22) Filed: Sep. 2, 2015

(65) Prior Publication Data

US 2016/0059039 A1 Mar. 3, 2016

Related U.S. Application Data

(60) Provisional application No. 62/044,585, filed on Sep. 2, 2014.

(51) Int. Cl.
| | |
|---|---|
| A61N 5/10 | (2006.01) |
| A61B 34/10 | (2016.01) |
| A61B 6/03 | (2006.01) |
| A61B 6/00 | (2006.01) |
| A61B 5/00 | (2006.01) |
| A61B 5/055 | (2006.01) |

(52) U.S. Cl.
CPC ............ *A61N 5/1039* (2013.01); *A61B 6/032* (2013.01); *A61B 6/5217* (2013.01); *A61B 34/10* (2016.02); *A61N 5/1031* (2013.01); *A61B 5/055* (2013.01); *A61B 5/7207* (2013.01); *A61B 5/748* (2013.01); *A61B 6/037* (2013.01); *A61B 6/542* (2013.01); *A61N 2005/1087* (2013.01)

(58) Field of Classification Search
CPC .... A61N 5/103; A61N 5/1037; A61N 5/1038; A61N 5/1039; A61N 5/1042–1045; A61N 5/1047; A61N 2005/1087
See application file for complete search history.

(56) References Cited

U.S. PATENT DOCUMENTS

2014/0206923 A1 * 7/2014 Hirayama ............ A61N 5/1031
600/1

* cited by examiner

*Primary Examiner* — Carrie R Dorna
(74) *Attorney, Agent, or Firm* — Quarles & Brady LLP

(57) ABSTRACT

The present invention provides a system and method for generating intensity modulated proton therapy plans. The method includes receiving a representation of a subject that includes information related to target and non-target volumes of interest, and computing, using the representation and a proton beam configuration that describes a number of beamlets and their respective arrangement, a dose distribution for each one of a plurality of uncertainty scenarios. The method also includes computing a robustness index for respective locations in the target volumes of interest using the dose distributions, and optimizing an objective function to determine a set of intensity weights for each beamlet in the proton beam configuration, wherein the objective function is based at least in part on deviations of the robustness indices from a prescribed robustness index. The method further includes generating a treatment plan using the determined intensity weights.

16 Claims, 4 Drawing Sheets

SYSTEM AND METHOD FOR ROBUST INTENSITY-MODULATED PROTON THERAPY PLANNING

CROSS-REFERENCE TO RELATED APPLICATIONS

This application claims the benefit of U.S. Provisional Patent Application Ser. No. 62/044,585, filed on Sep. 2, 2014, and entitled "SYSTEM AND METHOD FOR ROBUST INTENSITY-MODULATED PROTON THERAPY PLANNING."

STATEMENT REGARDING FEDERALLY SPONSORED RESEARCH

This invention was made with government support under CA168984 awarded by the National Institutes of Health. The government has certain rights in the invention.

BACKGROUND OF THE INVENTION

The field of the invention relates to systems and methods for ionizing radiation treatment. More particularly, the invention relates to systems and methods for intensity modulated proton therapy.

Lung cancer is the leading cancer killer worldwide, and about 30% to 40% of patients with locally advanced lung cancer require combined-modality treatment, including radiotherapy. However, with photon radiotherapy and concurrent chemotherapy, the 5-year survival is only about 15% for patients with stage III non-small cell lung cancer. Among those, about 50% experience local disease recurrence. Also, uncontrolled local disease may continue to seed to distant organs, resulting in distant metastasis and death. Hence, further improvements in survival of patients suffering from lung, and other types of cancer, require the safe delivery of higher radiation doses, which is not possible with photon radiotherapy.

Proton therapy approaches take advantage of the energy deposition profile of protons in tissue to provide highly conformal exposure of tumors while sparing organs-at-risk ("OAR"). Specifically, protons have a finite penetration depth in dependence of their energy, and the radiation dose delivered is maximum within a short distance of a proton's range, known as the Bragg peak. In particular, tissues located closer to the surface of a body receive less radiation dose compared to those at the Bragg peak. In addition, the dose profile drops dramatically beyond the Bragg peak, and hence tissues therein receive practically no radiation dose. As such, proton treatment systems make use of the dose deposition characteristics of protons in order to maximize tumor tissue coverage while minimizing dose to normal tissues as much as possible.

Unlike passive-scattering proton therapy ("PSPT") techniques, which includes scattering materials placed along the path of protons in order to provide lateral field sizes and depth of coverage useful for clinical applications, intensity-modulated proton therapy ("IMPT") uses magnetic steering of narrow proton beams, know as a beamlets, to deliver radiation dose to treatment target. Specifically, the energies and intensities of many individual beamlets, typically aimed at a target from multiple directions, are optimized using sophisticated computer algorithms that implement mathematically specified criteria, captured in what is known as an objective function. In the treatment of lung tumors, for example, this approach offers improved high-dose conformality when compared with PSPT, with better healthy tissue sparing in the mid- to low-dose range. Using such an objective function, an optimal compromise between adequate tumoricidal dose to a target and sparing of critical normal structures is achieved.

Several factors are known to change the dose received by target and normal structures as compared to the planned dose, thereby compromising the safety and efficacy of the treatment. For instance, inter-fractional variation in patient geometry, caused by tumor shrinkage, patient weight change, setup variation, proton range uncertainty, and so on, can cause significant differences in delivered dose distributions. Specifically, patient setup uncertainties can occur through the course of simulation and daily treatment. In addition, proton range uncertainty caused by tumor shrinkage, patient weight change, and computed tomography ("CT") number and stopping power ratio uncertainties may significantly alter dose to target and surrounding healthy, or non-target tissues. Unlike uncertainties caused by respiratory motion, patient setup and range uncertainties include systematic uncertainties that can affect the delivery of an intended dose throughout the course of multi-fractionated treatment. Some methods adopted in current practice that aim to address significant inter-fractional anatomy changes include adaptive replanning approaches. However, the adaptive re-plan is not robust to other uncertainties and only based on the most recent weekly CT imaging, while the anatomy change in a subsequent treatment fraction is not considered.

Intra-fractional respiratory motion may also cause significant changes in patient geometry during treatment and, consequently, in dose distribution delivered. Some optimization methods have been proposed to handle respiratory motion assuming that anatomy moves in exactly the same way during treatment sessions as it does during the simulation session. However, motion can vary from day to day, and such assumptions can considerably degrade the resulting dose distribution administered to a patient. Specifically, to account for respiratory motion, an internal gross target volume ("GTV") is conventionally formed to encompass the extent of GTV motion in all phases of a respiratory cycle using 4-dimensional ("4D") CT images. The GTV is then expanded to form an internal target volume ("ITV"), which includes an additional margin (e.g., 8 mm for lung patients) to account for subclinical microscopic disease. In current practice using PSPT, the change in tissue density due to respiratory motion is mitigated by use of averaged 4D CT and integrated-GTV (over all respiratory phases) density override, which includes the assignment of the maximum CT HU number from individual phases. Although this approach has been shown effective in preserving target coverage under the influence of respiratory motion for PSPT, its validity in IMPT has not been proved. Also, other techniques, such as breath-hold, gating, and tumor tracking methods are also commonly used to mitigate the effects of more substantial motion.

Generally, for intensity-modulated radiotherapy ("IMRT") approaches that provide treatment using photons, setup uncertainties are typically taken into account by adding isotropic margins to a clinical target volume ("CTV"), which reflects gross tumor and microscopic disease, to form a planning target volume ("PTV"). On the other hand, in PSPT, range and setup uncertainties are typically handled by adding lateral margins for setup uncertainties around the CTV and distal and proximal margins to account for range uncertainties. The PTV margin is chosen with the implicit assumption that the CTV will remain covered with the prescribed isodose surface with high probability (e.g., 95%) in the presence of the above described uncertainties. This is generally a good assumption for photons because the spatial distributions of photon dose are minimally perturbed by uncertainties. However, such approach of margin expansion may not be effective in IMPT due to the highly fluctuating nature of beamlet intensities and the resulting inhomogeneous dose distributions per beam in the target volume. Nevertheless, in the absence of suitable alternatives to assigning margins, the current practice in IMPT is to expand GTV to internal GTV and expand the CTV/ITV to form a PTV in a manner similar to the practice for photon therapy. As a result, the produced dose distributions are deficient in robustness and may cause IMPT dose distributions delivered to the patient to be significantly different from those prescribed, leading to unforeseen clinical consequences.

As many emerging proton treatment centers rely on pencil beam scanning technology, there is an increasing need for systems and methods for improved IMPT. Specifically, there is a need for systems and methods directed to quantifying a treatment plan's sensitivity to uncertainties, as well as mitigating the influence of such uncertainties, to deliver precise and predictable proton therapy with the highest clinical benefit.

SUMMARY OF THE INVENTION

The present invention overcomes the aforementioned drawbacks by providing a system and method directed to intensity modulated proton therapy ("IMPT") planning. Specifically, a novel approach for achieving improved tumor control and reduced normal tissue complications is introduced, whereby quantitative measures of robustness to multiple uncertainty scenarios are included in an optimization process for generating proton treatment plans. Treatment plans optimized in this manner produce margins that take into account various uncertainties encountered clinically, in contrast to previous approaches, which provide margin expansions that may not be effective due to the highly fluctuating nature of beamlet intensities and inhomogeneous dose distributions. As such, the present disclosure provides a methodology for mitigating the influence of uncertainties in the treatment plans generated, thus leading to significant benefit for patients treated with IMPT.

In one aspect of the present invention, a method for generating intensity modulated proton therapy plans is provided. The method includes receiving a representation of a subject that includes information related to target and non-target volumes of interest, and computing, using the representation and a proton beam configuration that describes a number of beamlets and their respective arrangement, a dose distribution for each one of a plurality of uncertainty scenarios. The method also includes computing a robustness index for respective locations in the target volumes of interest using the dose distributions, and optimizing an objective function to determine a set of intensity weights for each beamlet in the proton beam configuration, wherein the objective function is based at least in part on deviations of the robustness indices from a prescribed robustness index. The method further includes generating a treatment plan using the determined intensity weights.

In another aspect of the present invention, a system for generating intensity modulated proton therapy plans is provided. The system includes an input configured to accept a representation of a subject that includes information related to target and non-target volumes of interest. The system also includes at least one processor configured to compute, using the representation and a proton beam configuration that describes a number of beamlets and their respective arrangement, a dose distribution for each one of a plurality of uncertainty scenarios, and a robustness index for respective locations in the target volumes of interest using the dose distributions. The at least one processor is also configured to optimize an objective function to determine a set of intensity weights for each beamlet in the proton beam configuration, wherein the objective function is based at least in part on deviations of the robustness indices from a prescribed robustness index. The at least one processor is further configured to generate a treatment plan using the determined intensity weights.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Intensity-modulated proton therapy ("IMPT") has great potential to provide highly conformal tumor target coverage while sparing adjacent healthy organs. However, IMPT is highly sensitive to uncertainties, including patient setup, proton range in tissue, respiratory motion, tumor shrinkage, weight loss and so on. As a result, the dose distributions provided by conventional treatment planning systems may differ significantly from the dose distribution delivered within the patient, leading to unforeseen clinical consequences. To derive the highest clinical benefit, it is therefore important to quantify a plan's sensitivity to uncertainties, or a plan robustness, and to mitigate the influence of uncertainties in the plan generation process in order to deliver particle therapy precisely and predictably.

Several robustness quantification approaches have been attempted. However, these methods either provide only qualitative measure of a plan robustness or are computationally challenging. As such, the present invention recognizes a need for a robustness index that can be based on a single numerical value to indicate plan robustness.

Additionally, different optimization methods have also been proposed. Although such optimization methods were shown to be effective in rendering IMPT plans less sensitive to uncertainties, in many cases it may be desirable for treatment planners to control the tradeoff between plan robustness and normal tissue sparing. For example, one proposed method to control a plan robustness included robustness in multi-criteria optimization ("MCO") approach. However, MCO is not an optimization method conventionally used in radiation therapy and requires numerous base plans. Thus, previous optimization approaches are lacking since they do not explicitly allow for controlling a plan's robustness, or because they are computationally cumbersome. As a result, the present invention recognizes a need for a robust optimization method that includes the capability to explicitly control plan robustness, using, as one example, conventional nonlinear programming.

Figure 1:
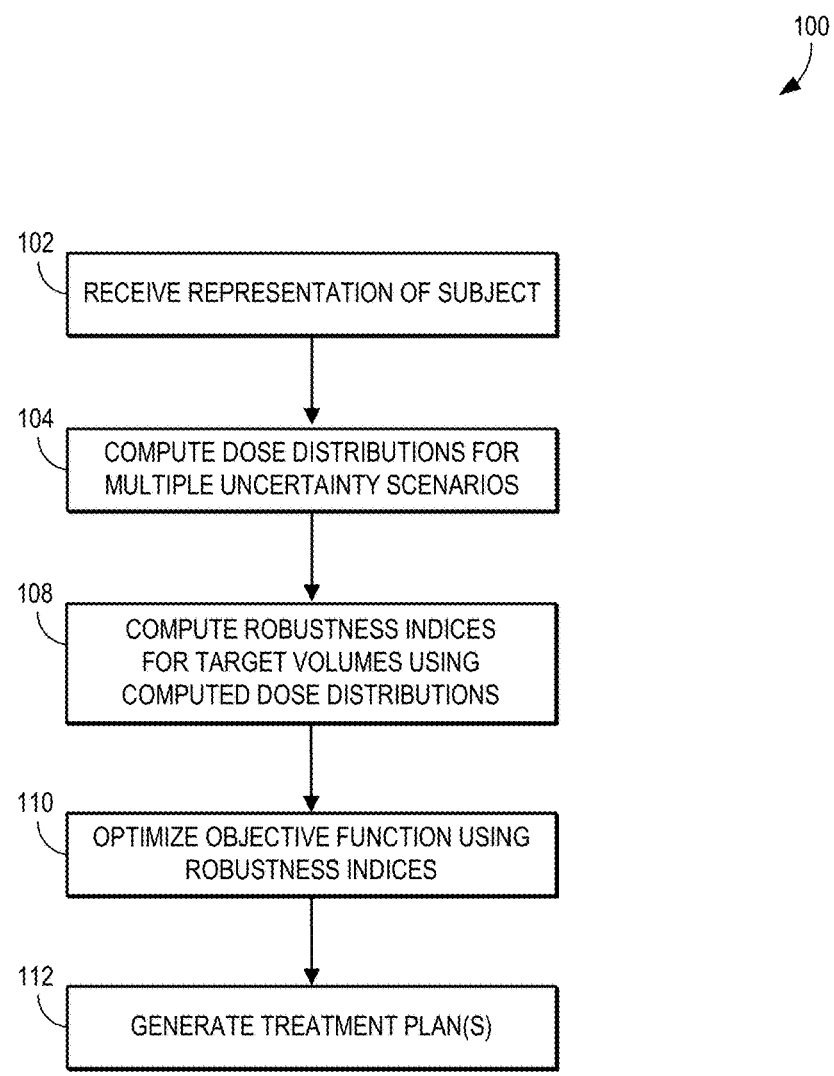
FIG. 1 is a flowchart setting forth the steps of an exemplary proton treatment planning method in accordance with the present disclosure.

Turning to FIG. 1, a flowchart is shown setting forth the steps of an example method for proton treatment planning in accordance with the present disclosure. The process 100 may begin at process block 102, whereby a representation of a subject is received. The representation may include any number of images acquired from a subject, including images acquired during a treatment simulation protocol. Specifically, such images may be acquired using a number of imaging modalities, including computed tomography ("CT"), magnetic resonance ("MR"), positron emission tomography ("PET"), proton CT, and other imaging modalities, which may provide temporal information as well. In addition, the representation may also include information related to target and non-target volumes of interest ("VOI"). This may include contours of diseased and normal tissue structures, which may be identified by a clinician, or as a result of a segmentation algorithm.

A common strategy in IMPT optimization for generating treatment plans involves first computing dose contributions per unit intensity of all proton beamlets associated with the radiation treatment to each voxel in a VOI, which may include both target and critical structures, prior to optimization. Such computations, which can be performed using any appropriate pencil-beam algorithm, are captured in what is known as an influence matrix ("IM"). These computations allow for the separation of complex dose calculations from the optimization process. Subsequently, during optimization, weights are determined in accordance with desired clinical objectives, in order to determine optimized dose distributions. This approach has the advantage of speed and efficiency since the actual dose distribution can be updated quickly using the IM.

In this manner, at process block 104, a number of dose distributions may be computed based on multiple uncertainty scenarios. In particular, using a representation of the subject, as described, and a prescribed, or determined, proton beam configuration that describes a number of proton beamlets and their respective arrangement relative to the subject, multiple dose distributions may be calculated. In some aspects, at process block 104, uncertainty scenarios may include inter-fractional setup uncertainties. For instance, setup uncertainties may be considered to be random and may be modeled by calculating the dose distribution for any respiratory phase by shifting the isocenter of a patient's CT image in antero-posterior ("AP"), superior-inferior ("SI"), and lateral, or right-left, ("RL") directions by any margins, such as, margins commonly used for defining a planning target volume ("PTV"). This yields 6 dose distributions plus 1 nominal dose distribution and the corresponding IMs.

Other uncertainty scenarios included at process block 104 may include proton range uncertainties. Specifically, proton range uncertainties for each patient can be generally systematic and propagate through the whole course of the treatment, but they are usually random for a patient population. As such, they may be modeled by calculating dose distribution for any respiratory phase by scaling stopping power ratios by say, −3.5% and +3.5%, although other values are possible, to generate dose distributions and IMs corresponding to maximum and minimum proton ranges, respectively.

The above-described example uncertainty scenarios, including dose distributions for nominal, minimum, and maximum proton ranges, as well as dose distributions whereby the isocenter of the patient from the nominal position is rigidly shifted in the AP, SI, and RL directions, respectively, result in 21 dose distributions (7 per proton range). However, any number dose distributions may be computed at process block 104 in dependence of a desired number of uncertainty scenarios.

At process block 108, a number of robustness indices, such as root-mean-square deviations, may be computed for respective voxels, or locations in volumes of interest within a patient using dose distributions computed at process block 104, as will be described. Specifically, each voxel dose may be represented using $D_{i_k}^m$, where $i_k$ is the corresponding voxel on a respiratory phase k, such as an end-expiration phase, on say a CT image and, and m denotes an uncertainty scenario, as described. For example, a total of 10 respiratory phases from a 4D simulation CT may be utilized, although other values are possible.

As described, each voxel dose can be obtained from the relation $$D_{i_k}^m = \sum_j IM_{i_k}^m \omega_j^2$$

where $\omega_j^2$ is a nonnegative intensity weight of proton beamlet, j, utilized in the plan, and $IM_{i_k}^m$ is the influence matrix for the respiratory phase k under the $m^{th}$ uncertainty scenario, calculated, for example, using an engine configured for pencil proton beams of finite size.

Then accumulated doses $\langle D_i^m \rangle$ for each uncertainty scenario may be summed onto the single reference respiratory phase weighted by a nominal motion probability mass function ("pmf") as follows, $$\langle D_i^m \rangle = \Sigma_k D_{i_k}^m pmf_k^0. \qquad (1).$$

The motion probability mass function $pmf_k$ models motion of a subject's anatomy and includes a nominal probability mass function surrounded by upper and lower error bars, namely $pmf_k = pmf_k^0 \pm \Delta pmf_k$. The nominal probability mass function, $pmf_k^0$, can be thought of as the mean of the relative amount of time spent in different phases of the breathing cycle, while the error bars describe the extent of the variability. This information could be acquired from an internal marker, such as a fluoroscopic marker, an external marker such as by using a real-time position management ("RPM") system, or both. Specifically, RPM data can be easily obtained on different days and can be used to estimate the variability in breathing from fraction to fraction of the individual patient. Additionally, the 4D dose accumulation may be facilitated by use of a symmetric force demon registration software to establish point-to-point correspondence, or deformation vector, to map the target respiratory phase to the reference phase (i.e., from $i_k$ to i). This method can more effectively handle nonlinear image deformation, which could be very important in patients with lung cancer. Image registration may be performed with the CT coordinates to improve accuracy. Additionally, to speed up the image registration and meet the memory requirement, a multi-resolution approach may be used in the image registration process. Moreover, a trilinear method can be used to interpolate the dose calculation from the CT coordinates to the coarser dose calculation coordinates.

As described, nominal dose distributions, or dose distributions that do not consider uncertainties, may not represent the dose distributions actually realized in the presence of uncertainties. Therefore, when generating or comparing plan qualities under the influence of uncertainties, it is important to incorporate the effect of uncertainties on the planned dose distribution. This process, in general, can be referred to as robustness quantification. In theory, it is possible to examine all uncertainty situations, but it would require significant computation time and data processing effort to evaluate plans under all realizable perturbed doses from the uncertainties. Therefore a root-mean-square deviation ("RMSD"), or robustness index, is utilized at process block 108 as a measure of robustness of dose for each voxel in a VOI as a result of multiple uncertainty scenarios. As will be described, this allows for the capability to explicitly control plan robustness during the optimization process, while providing a simplified method for comparing plan robustness. In particular, radiotherapy plans not sensitive to uncertainties are termed "robust plans."

Specifically, RMSD index values for voxels in a VOI can be calculated as the square root of the sum square of the differences between the 4D dose, $\langle D_i^m \rangle$, accumulated onto a reference CT at each voxel of the reference CT (see Eqn. (1)), calculated, say, under 8 or more uncertainty scenarios and a nominal scenario, and the mean dose of those 9 doses, as follows:

$$RMSD_i = \sqrt{\frac{\sum_{m=1}^{9}(\langle D_i^m \rangle - \overline{D_i})^2}{9}} ; \quad (2)$$

where, $$\overline{D_i} = \frac{\sum_{m=1}^{9}\langle D_i^m \rangle}{9}. \quad (3)$$

Figure 2:
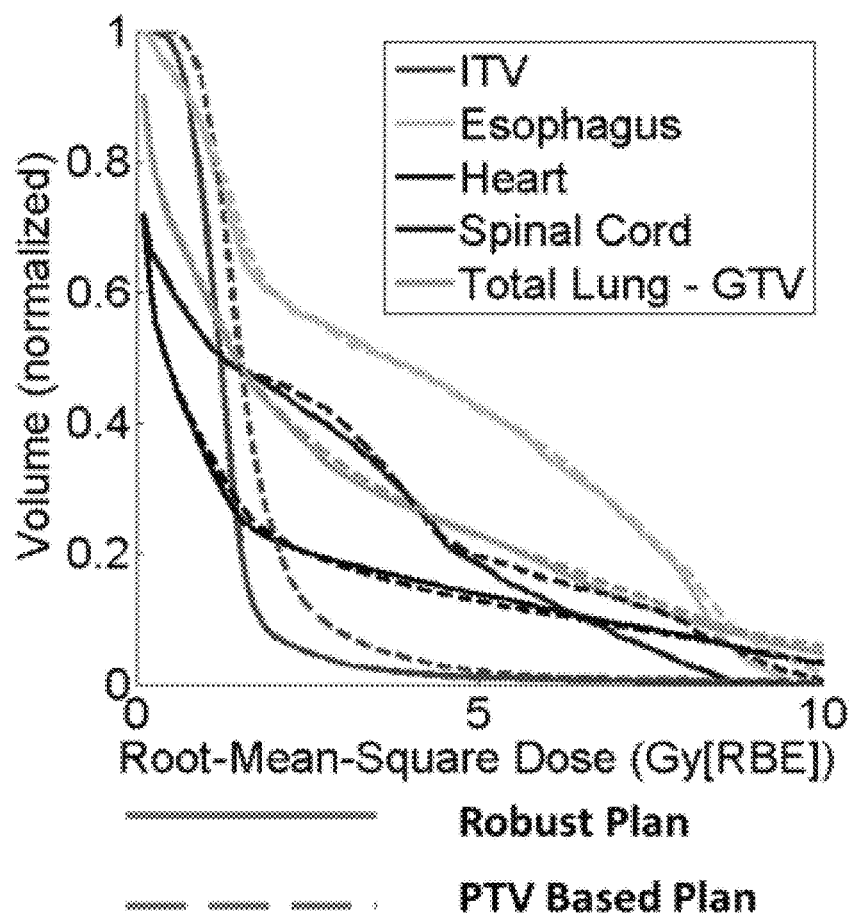
FIG. 2 shows example root-mean-square dose-volume histograms ("RVHs") generated in accordance with the present disclosure as compared to traditional planning target volume ("PTV")-based planning.

In some aspects, RMSD index values computed according to Eqns. (2) and (3) may be used to construct a number of root-mean-square dose-volume histograms ("RVHs"), which provide an indication of dose deviations for particular volumes of interest. For example, as shown in FIG. 2, RVH plots may capture the overall effect of uncertainties on the dose to a volume of interest that is analogous to dose volume histograms ("DVHs") commonly utilized for assessing the doses to various structures. In this manner, a comparison may be performed with respect to plans generated using different optimization methods. For instance, as shown in FIG. 2, the area of an internal target volume ("ITV") robustly optimized dose distribution in accordance with the present disclosure, as will be described, is smaller than that of an optimized plan achieved using a PTV-based approach.

Furthermore, to simplify a RVH comparison between the robustness of different plans, an area under the curve ("AUC") value may be calculated for each RVH curve of interest. This gives a single numerical measure of a plan's robustness for a given VOI that can be easily incorporated into paired statistical tests for comparison. For instance, the smaller an AUC value, the more robust a plan may be for any given structure. Such robustness quantification metrics based on computed RMSD values can be applied in the clinic to help physicians and physicists judge whether IMPT plans are acceptable, or advantages of certain plans over others.

Returning to FIG. 1, at process block 110, an objective function is optimized to determine a set of intensity weights for each beamlet in a particular proton beam configuration. Specifically, a quadratic objective function is optimized to generate IMPT plans using 4D accumulated nominal doses $\langle D_i^0 \rangle$ as follows:

$$F^{4D}(\omega_j) = \sum_{i \in CTV} p_{CTV}(\langle D_i^0 \rangle - D_{0,CTV})^2 + \quad (4)$$
$$\sum_{i \in OARs} p_{OARs} H(\langle D_i^0 \rangle - D_{0,OARs})(\langle D_i^0 \rangle - D_{0,OARs})^2 +$$
$$\sum_{i \in CTV} p_{CTV,Robust} H(RMSD_i - RMSD_0)(RMSD_i - RMSD_0)^2;$$

where the p terms denote the penalty weights of the corresponding structures and $D_0$ terms are the prescribed doses for the corresponding organs. The Heaviside function $H(D_i - D_0)$ is defined conventionally, with a value of unity if its argument is greater than zero and a value of zero if its argument is less than or equal to zero. Dose-volume constraints may be incorporated in the two terms of Eqn. (4) using previously reported methods. Note that the optimization target is designated to be the clinical target volume ("CTV"). In the described 4D optimization method, the target of the individual phases of the 4D CT deliberately receives non-uniform doses, but the accumulated dose of all phases to the target is uniform with the value of the prescription dose. As mentioned, robustness measures are included into the optimization process by incorporating RMSD index values into the objective function, as shown in Eqn. (4), where $RMSD_0$ represents the prescribed RMSD value for each voxel in the CTV, and the term $p_{CTV,Robust}$ is a user-defined parameter that may be used to control the relative importance of the plan robustness in the total objective function. As shown in Eqn. (4), plan robustness is included into the optimization process by directly penalizing the deviation of the per voxel RMSD from the prescribed RMSD. In some aspects, additional RMSD terms related to the organs-at-risk (OARs) could be added to control the robustness for the related OARs if needed.

Using the above-described optimization process that determines optimized dose distributions, at process block 112, any number of proton treatment plans may be generated. For instance, the above-described optimization process may be utilized in a planning or replanning proton treatment protocol. Although the above-described robust optimization method could allow proton plans generated to be more robust despite uncertainties, the extent of a plan's robustness to uncertainties might not be explicitly controlled by a treatment planner. Therefore, an approach similar to how dose-volume constraints are used to explicitly control the curves of DVH (and therefore plan quality) can be adopted. Specifically, RVH curves, and therefore plan robustness, may be explicitly controlled by including root-mean-square volume constraints ("RVC") in the optimization process.

Figure 3:
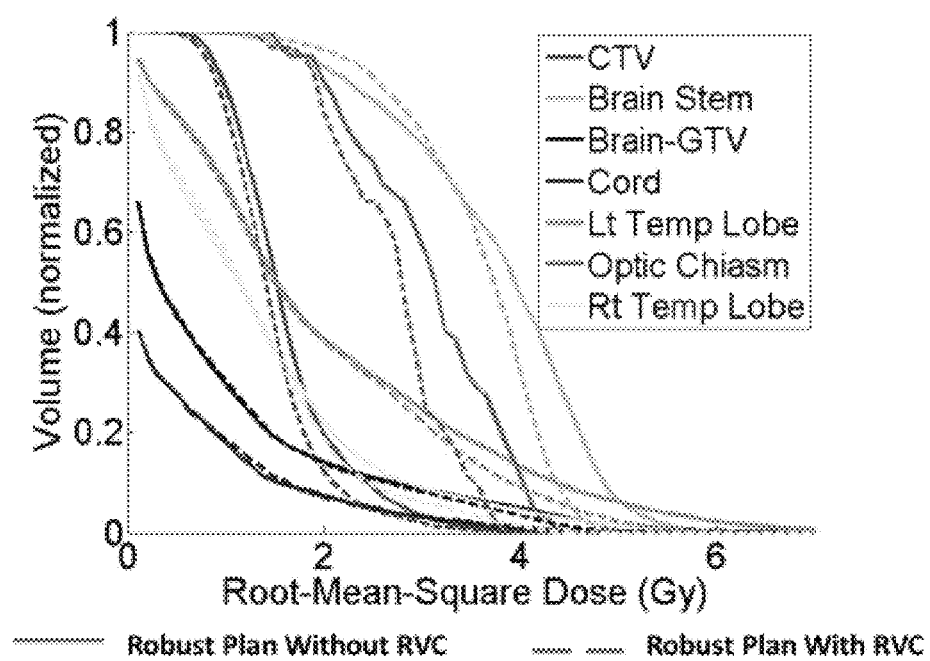
FIG. 3 illustrates example RVHs generated in accordance with the present disclosure with and without root-mean-square volume constraints ("RVC") included in the optimization process.

By way of example, FIG. 3 shows respective RVH curves of several tissue structures for two IMPT plans generated in a manner described. Specifically, a comparison between one plan optimized with an RVC, namely no more than 10% of the CTV volume having a RMSD value larger than 2 Gy, and the other without such constraint, is shown. The AUC value for the CTV RVH curve without constraint is 15.01, and that of the CTV RVH curve with a constraint is 13.56. As shown, providing RVC enables control of how insensitive a plan may be in the face of uncertainty. Particularly, not only can a robust plan be obtained via an optimization process as provided by the present disclosure, but also explicit control can be achieved with respect to how insensitive the robust plan may be in the face of uncertainty via robust optimization using RVCs.

In addition to uncertainties due to patient setup, proton beam range, and regular respiratory motion, additional uncertainties in IMPT may include irregular respiratory motion, and patient anatomy changes due to tumor shrinkage, patient weight loss, and so on. Therefore, in order to enhance IMPT plan robustness further, in some aspects, these additional uncertainties may also be addressed using the approach provided by the present disclosure.

In particular, a 4D optimization process may be performed with proton range and setup uncertainties, as described, and considered to be a zeroth order solution, resulting in a nominal beamlet intensity map, $\omega_{j,0}^2$. To find a worst-case perturbed probability mass function, $pmf_k^1$, a second optimization step using the nominal intensity map $\omega_{1,0}^2$ may then be performed to find a solution for the fraction of time spent in each respiratory phase, in which target voxels would spend as much time as possible in the phase receiving a low dose and as little time as possible in the phase receiving a high dose, while the cumulative doses of all phases of the target voxels still satisfy the constraints of the target. An updated worst-case probability mass function, $pmf_k^u$, may be attained using $pmf_k^u = pmf_k^0 + pmf_k^1$, which indicates the fraction of time spent in phase k during an irregular breathing cycle in the worst-case scenario (first-order perturbation). The "error bar" $\Delta pmf_k$ derived from RPM data may be used to constrain for this second optimization.

A third optimization step may subsequently be performed, minimizing the same objective function of Eqn. (4), but with the nominal probability mass function replaced by the updated worst-case probability mass function. Specifically, an updated intensity map is derived, as a way of providing a correction step. The nominal/updated accumulated dose distribution may then be calculated using the nominal/updated probability mass function and nominal/updated intensity map, respectively. A relative maximum dose difference ratio between these two accumulated dose distributions may then be calculated to ensure that a predetermined convergence threshold is met; otherwise, the second and third optimization steps may be repeated iteratively, with the computed beamlet intensity map derived from the third optimization step provided as input to the second optimization step.

Additionally, inter-fractional changes in anatomy (e.g., tumor shrinkage, patient weight change, and so on), when found to be clinically significant, as evidenced by meeting specified dosimetric constraints, are generally accounted for through adaptive replanning. However, in certain cases, there may be variation in the anatomy during the period between the most recent treatment plan and the implementation of the next adaptive plan. As such, it would be advantageous for a robust optimizer to achieve a more "optimal" plan if information related to how the anatomy evolves during this period of time is provided. Therefore, following the same ideas underlying demon registration techniques, the movement of tissues, such as tumor tissues, could be described using an "optic flow" concept described using the Navier-Stokes Equations in hydrodynamics. Specifically the dynamics of tumor tissues can be modeled as the following partial differential equation:

$$\partial n/\partial t = \gamma_1 n - (\alpha D + \beta D^2) n + \nabla \cdot \gamma_2 \nabla n \qquad (5);$$

where n(x, y, z, t) represents the tumor cell number density derived from the CT images, t is time, and (x, y, z) are the spatial coordinates in the RL, AP, and SI directions, respectively. The first term on the right-hand side of Eqn. (5) is the cell repopulation term. The second term on the right-hand side depicts the cell killing based on the standard linear-quadratic model for a known radiation dose D per fractionation (mostly 2 Gy per fractionation). The third term depicts the tumor cell number local migration term that is analogous to the diffusion term in fluid hydrodynamics. The parameters $\gamma_1$, $\alpha$, $\beta$, $\gamma_2$ may be functions of time and position (x, y, z, t) and possibly functions of tumor characteristics such as tumor physiology, tumor size, tumor stage, and patient health.

One efficient way to solving Eqn. (5) includes using a parallelized solver similar to hydrodynamics approach. Specifically, an initial guess for those parameters could be derived in an optimization process that minimizes the deviation between a "predicted" tumor cell number density and a tumor cell number density measured from, say, a next available weekly CT image. The whole process is analogous to the approach used in image registration techniques. Specifically, the parameters of Eqn. (5) could be further tuned iteratively using sequential weekly CTs. Given a very efficient partial differential equation solver, weekly CTs of a patient population will be used to construct a "class solution" as a good initial guess for parameters $\gamma_1$, $\alpha$, $\beta$, $\gamma_2$ categorized by tumor physiology, tumor size, tumor stage, and patient health quantified, for example, using the Karnofsky Performance Status scale.

For an individual patient, it may be advantageous to have the patient-specific tumor evolution process described by Eqn. (5) using patient-specific $\gamma_1$, $\alpha$, $\beta$, $\gamma_2$ parameter values. This may be achieved using dynamic programming techniques, such as backward recursive solution of Bellman's equations. For instance, during an adaptive re-planning process of an individual patient's treatment course, parameters with the initial values obtained from the "class solution" can be continuously refined. The "patient-specific" parameters can then be obtained after some weekly CT images, since ever more tumor evolution information becomes available. The adaptive robust replanning, in accordance with the present disclosure, based on patient-specific parameters in Eqn. 4 may lead to "personalized" adaptive proton therapy.

Figure 4:
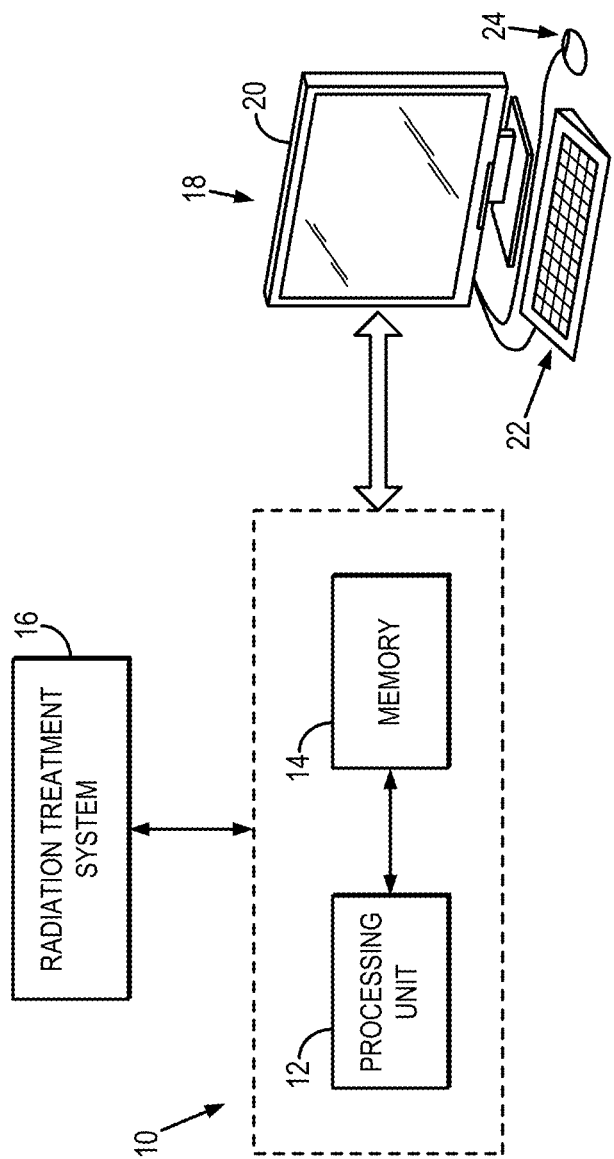
FIG. 4 is a schematic illustration of a system for use in accordance with the present disclosure.

The methods provided by the present disclosure can be suitably implemented using a radiation treatment planning system, or any other suitable computing system. Referring now to FIG. 4, an example of such a radiation treatment planning system 10 is illustrated. The radiation treatment planning system 10 is preferably in communication with one or more radiation treatment systems 12, which may include any suitable proton radiation treatment system.

The radiation treatment planning system 10 generally includes a memory 14 that is operably coupled to a processor unit 16. As an example, the memory 14 can include a plurality of memory elements, or can include a single memory element. In general, the memory 14 is configured to store patient data, including representations, or images acquired from patient, such as CT, MR, or PET images, as well as information related to target and non-target volumes of interest, and so on.

As an example, the processor unit 16 can be a commercially available computer processor. In addition to other processing tasks, the processor unit is configured to carry out one or more of the steps of the methods described above. In particular, to meet the challenging memory requirements and perform the specific aims efficiently for clinical utility, a hierarchical 2-level hybrid parallelization processing scheme may be configured for use with the radiation treatment planning system 10. The hierarchical hybrid parallelization scheme is composed of 2 levels of parallelization: 1) memory-distributed parallelization via message-passing interface between different computing nodes and 2) GPU-based memory-shared parallelization within one node to speed up the optimization and efficiently address the demanding memory requirement problem. This hierarchical hybrid parallelization scheme would be able to maximize the advantages and minimize the disadvantages of memory-distributed parallelization (unlimited memory, but with the bottleneck from message passing between the different nodes, which restrains the optimization speed) and GPU-based memory-shared parallelization (significantly speeding computation but with limited memory). In this manner, at least 200 times speed-up is expected, making the goal of treatment planning, say for a complicated lung case for IMPT, achievable within minutes.

In addition, preferably, the radiation treatment planning system 10 includes, or is otherwise in communication with, a user interface 18. As an example, the user interface 18 provides information to a user, such as a medical physicist. For example, the user interface 18 can include a display 20 and one or more input devices, such as a keyboard 22 and mouse 24.

In summary, IMPT provides a highly conformal method for proton radiotherapy delivery that can improve treatment outcomes and decrease morbidity. Although protons can potentially deliver much higher doses to tumors, as compared with photon-based treatments, while keeping dose to normal tissues low, it is more sensitive to uncertainties. This could lead to local treatment failure and normal tissue over-dose. For example, many lung cancer patients succumb to the disease after radiation therapy due to local disease recurrence. Over-irradiating critical normal tissues can increase the risk of severe adverse effects, such as esophagitis, myelitis, brachial plexopathy, pneumonitis, pulmonary fibrosis, cardiac toxicity, and secondary cancers. Better preservation of critical normal tissues would decrease morbidity and result in better quality of life for patients. In addition, possible severe toxic effects compromise the delivery of cancer radiotherapy, because dose reductions necessary to allow for the resolution of side effects reduce the effectiveness of the therapy.

Therefore, the present disclosure provides an approach that would ensure safety and efficacy of IMPT. Using a system and method as described herein, the capabilities of radiation treatment using protons can be fully exploited, improving patient outcomes and increasing survival. Specifically, using the methodology provided by the present disclosure, the influence of residual respiratory motion, along with setup and proton range uncertainties may be mitigated in IMPT. Therefore, such planning approach may have a large, immediate clinical impact because several centers already treat or plan to treat lung cancer patients using breath-hold or beam gating. It is also anticipated that systems and methods, as described, may also be readily applicable to other cancer patients, including those with head and neck, or particularly those in which respiratory motion is problematic, such as patients with esophagus and liver cancers. Using the approach provided herein, it is possible to generate IMPT plans as reliable as those for photon therapy, significantly improving normal tissue sparing of IMPT. This will eliminate concerns and reluctance of practitioners to apply this highly promising treatment modality (IMPT) clinically, thus creating a far-reaching benefit for cancer patients.

The present invention has been described in terms of one or more preferred embodiments, and it should be appreciated that many equivalents, alternatives, variations, and modifications, aside from those expressly stated, are possible and within the scope of the invention.

I claim:
1. A computer-implemented method for generating an intensity modulated proton therapy plan, the steps of the method comprising:
    (a) providing a representation of a subject that includes information related to target and non-target volumes of interest to a treatment planning system;
    (b) providing to the treatment planning system, a proton beam configuration that describes a number of beamlets and their respective arrangement;
    (c) computing with the treatment planning system, a dose distribution for each one of a plurality of uncertainty scenarios, wherein the dose distribution is computed based on the provided representation of the subject and the provided proton beam configuration;
    (d) computing with the treatment planning system, a robustness index for respective locations in the target volumes of interest using the computed dose distributions;
    (e) optimizing an objective function with the treatment planning system to determine a set of intensity weights for each beamlet in the proton beam configuration, wherein the objective function is based at least in part on deviations of each computed robustness index from a prescribed robustness index; and
    (f) generating a treatment plan with the treatment planning system using the intensity weights determined by optimizing the objective function.

2. The method of claim 1, wherein the representation includes at least one image of the subject acquired using one of x-ray computed tomography ("CT"), magnetic resonance imaging ("MRI"), positron emission tomography ("PET"), or proton CT.

3. The method of claim 1, wherein the plurality of uncertainty scenarios include a combination of a series of setup uncertainty scenarios, a series of proton range uncertainty scenarios, and a series of motion uncertainty scenarios.

4. The method of claim 1, wherein the robustness index for each location is defined according to:

$$RMSD_i = \sqrt{\frac{\sum_{m=1}^{9}(\langle D_i^m \rangle - \overline{D_i})^2}{9}}$$

where $\langle D_i^m \rangle$ is an accumulated dose for location, i, and for an uncertainty scenario, m, and wherein $$\overline{D_i} = \frac{\sum_{m=1}^{9} \langle D_i^m \rangle}{9}.$$

5. The method of claim 4, wherein the objective function is defined as:

$$F^{4D}(\omega_j) = \sum_{i \in CTV} p_{CTV}(\langle D_i^0 \rangle - D_{0,CTV})^2 +$$
$$\sum_{i \in OARs} p_{OARs} H(\langle D_i^0 \rangle - D_{0,OARs})(\langle D_i^0 \rangle - D_{0,OARs})^2 +$$
$$\sum_{i \in CTV} p_{CTV,Robust} H(RMSD_i - RMSD_0)(RMSD_i - RMSD_0)^2$$

where $p_{CTV}$, $p_{OARs}$, and $p_{CTV,Robust}$ are penalty weights, $D_{0,CTV}$, $D_{0,OARs}$, are prescribed doses for respective tissues, $RMSD_0$ is the prescribed robustness index, $RMSD_i$ is the robustness index value for each location i in the target volumes of interest, and $H(D_i - D_0)$ is a Heavyside function with value of unity if an argument is greater than zero and value of zero if the argument is less than or equal to zero.

6. The method of claim 4, further comprising generating a report that indicates a robustness of the treatment plan generated in step (f).

7. The method of claim 6, wherein generating the report includes generating a plurality of root-mean-square volume histograms ("RVHs") using the robustness index for respective locations in the target volumes of interest computed at step (d) and displaying the RVHs in the generated report.

8. The method of claim 7, wherein generating the report includes computing an area under the curve ("AUC") metric based on the plurality of RVHs and displaying the AUC metric in the generated report.

9. A treatment planning system for use in intensity-modulated proton therapy, comprising:
   a memory for storing thereon a representation of a subject and a proton beam configuration, wherein the representation of the subject includes information related to target and non-target volumes of interest and the proton beam configuration describes a number of beamlets and their respective arrangement;
   a processor for receiving the representation of the subject and the proton beam configuration from the memory and for generating a treatment plan based on the representation of the subject and the proton beam configuration;
   a display for displaying the treatment plan; and
   wherein the processor generates the treatment plan by:
      computing a dose distribution for each one of a plurality of uncertainty scenarios, wherein each dose distribution is computed based on the representation of the subject and the proton beam configuration;
      computing a robustness index for respective locations in the target volumes of interest using the computed dose distributions;
      optimizing an objective function to determine a set of intensity weights for each beamlet in the proton beam configuration, wherein the objective function is based at least in part on deviations of each computed robustness index from a prescribed robustness index; and
      generating the treatment plan using the intensity weights determined by optimizing the objective function.

10. The treatment planning system of claim 9, wherein the representation of the subject includes at least one image of the subject acquired using one of x-ray computed tomography ("CT"), magnetic resonance imaging ("MRI"), positron emission tomography ("PET"), or proton CT.

11. The treatment planning system of claim 10, wherein the plurality of uncertainty scenarios include a combination of a series of setup uncertainty scenarios, a series of proton range uncertainty scenarios, and a series of motion uncertainty scenarios.

12. The treatment planning system of claim 10, wherein the robustness index for each location is defined according to:

$$RMSD_i = \sqrt{\frac{\sum_{m=1}^{9}(\langle D_i^m \rangle - \overline{D_i})^2}{9}}$$

where $\langle D_i^m \rangle$ is an accumulated dose for location, i, and for an uncertainty scenario, m, and wherein $$\overline{D_i} = \frac{\sum_{m=1}^{9} \langle D_i^m \rangle}{9}.$$

13. The treatment planning system of claim 12, wherein the objective function is defined as:

$$F^{4D}(\omega_j) = \sum_{i \in CTV} p_{CTV}(\langle D_i^0 \rangle - D_{0,CTV})^2 +$$
$$\sum_{i \in OARs} p_{OARs} H(\langle D_i^0 \rangle - D_{0,OARs})(\langle D_i^0 \rangle - D_{0,OARs})^2 +$$
$$\sum_{i \in CTV} p_{CTV,Robust} H(RMSD_i - RMSD_0)(RMSD_i - RMSD_0)^2$$

where $p_{CTV}$, $p_{OARs}$, and $p_{CTV,Robust}$ are penalty weights, $D_{0,CTV}$, $D_{0,OARs}$, are prescribed doses for respective tissues, $RMSD_0$ is the prescribed robustness index, $RMSD_i$ is the robustness index value for each location i in the target volumes of interest, and $H(D_i - D_0)$ is a Heavyside function with value of unity if an argument is greater than zero and value of zero if the argument is less than or equal to zero.

14. The treatment planning system of claim 12, wherein the processor further generates at least one metric that indicates a robustness of the treatment plan.

15. The treatment planning system of claim 14, wherein the at least one metric includes a plurality of root-mean-square volume histograms ("RVHs") computed using the robustness index for respective locations in the target volumes of interest.

16. The treatment planning system of claim 15, wherein the at least one metric further includes an area under the curve ("AUC") metric computed based on the plurality of RVHs.

* * * * *